(12) United States Patent
Fogwill et al.

(10) Patent No.: US 10,359,403 B2
(45) Date of Patent: Jul. 23, 2019

(54) CARBON DIOXIDE BASED CHROMATOGRAPHY SYSTEMS INCLUDING MULTIPLE PRESSURE CONTROL DEVICES

(71) Applicant: Waters Technologies Corporation, Milford, MA (US)

(72) Inventors: Michael O. Fogwill, South Grafton, MA (US); Joshua A. Shreve, Franklin, MA (US); Michael Eggertson, Natick, MA (US); Thomas S. McDonald, Littleton, MA (US); Joseph D. Michienzi, Plainville, MA (US); Abhijit Tarafder, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 15/909,275

(22) Filed: Mar. 1, 2018

(65) Prior Publication Data
US 2018/0252685 A1     Sep. 6, 2018

Related U.S. Application Data

(60) Provisional application No. 62/466,552, filed on Mar. 3, 2017.

(51) Int. Cl.
*G01N 30/32* (2006.01)
*G01N 30/72* (2006.01)
(Continued)

(52) U.S. Cl.
CPC .......... *G01N 30/32* (2013.01); *B01D 15/163* (2013.01); *B01D 15/40* (2013.01); *G01N 30/34* (2013.01);
(Continued)

(58) Field of Classification Search
CPC .... G01N 30/32; G01N 30/36; G01N 30/7233; G01N 2030/326; B01D 15/163; B01D 15/40
See application file for complete search history.

(56) References Cited

U.S. PATENT DOCUMENTS 4,628,743 A * 12/1986 Miller, Jr. ............. G01F 1/7044
                                                    73/204.25
4,871,453 A * 10/1989 Kumar ................... G01N 30/28
                                                    210/198.2
(Continued)

FOREIGN PATENT DOCUMENTS

WO      2015/023533 A1    2/2015

OTHER PUBLICATIONS

Guiochon, et al. "Fundamental Challenges and Opportunities for Preparative Supercritical Fluid Chromatography", Journal of Chromatography A, 1218:8, 1037-1114 (2010).
(Continued)

*Primary Examiner* — Justin N Olamit
(74) *Attorney, Agent, or Firm* — Womble Bond Dickinson (US) LLP; Deborah M. Vernon; Heath T. Misley (57) ABSTRACT

The present disclosure relates to methodologies, systems and apparatus for controlling pressure in a $CO_2$-based chromatography system. A first pressure control element is located downstream of a $CO_2$-based chromatography system and is disposed to control pressure within the column. A split restrictor is located downstream of the primary pressure control element and is disposed to divert a portion of the mobile phase flow to a detector. A second pressure control element is located downstream of the split restrictor and is disposed to control pressure at the restrictor. While the first pressure control element executes a pressure-controlled gradient separation, the second pressure control element maintains a constant pressure at the restrictor. During a composition-programmed gradient separation, the second control element maintains a constant pressure at the split restrictor while the first pressure control element maintains a constant average density across the column.

22 Claims, 6 Drawing Sheets

(51) Int. Cl.
*G01N 30/34* (2006.01)
*B01D 15/16* (2006.01)
*B01D 15/40* (2006.01)

(52) U.S. Cl.
CPC ... *G01N 30/7233* (2013.01); *G01N 2030/326* (2013.01)

(56) References Cited

U.S. PATENT DOCUMENTS

| | | | |
|---|---|---|---|
| 6,358,414 B1 * | 3/2002 | Maiefski | B01D 15/08 137/334 |
| 8,877,051 B2 * | 11/2014 | Fogelman | G01N 30/82 210/143 |
| 9,694,301 B2 * | 7/2017 | Choikhet | G01N 30/463 |
| 2015/0101393 A1 * | 4/2015 | Fogwill | G01F 1/76 73/23.31 |
| 2015/0301000 A1 * | 10/2015 | Fogwill | G01N 30/68 436/160 |
| 2016/0018367 A1 | 1/2016 | Fogwill et al. | |
| 2016/0069845 A1 | 3/2016 | Fogwill et al. | |
| 2016/0375376 A1 * | 12/2016 | Wikfors | B01D 15/163 210/198.2 |

OTHER PUBLICATIONS

International Search Report and Written Opinion relating to corresponding Application No. PCT/IB2018/051325 completed on May 28, 2018 and dated Jun. 8, 2018.

* cited by examiner

FIG. 1

(Prior Art)

CARBON DIOXIDE BASED CHROMATOGRAPHY SYSTEMS INCLUDING MULTIPLE PRESSURE CONTROL DEVICES

RELATED APPLICATIONS

This application claims the benefit of U.S. Provisional Patent Application 62/466,552 filed on Mar. 3, 2017 titled "CARBON DIOXIDE BASED CHROMATOGRAPHY SYSTEMS INCLUDING MULTIPLE PRESSURE CONTROL DEVICES," the contents of which are incorporated herein by reference in its entirety.

TECHNICAL FIELD

The present disclosure relates to techniques for controlling pressure in carbon dioxide-based chromatography systems. The present disclosure also relates to methodologies, systems and apparatus for controlling pressure downstream of a chromatography column.

BACKGROUND OF THE TECHNOLOGY

Chromatography involves the flowing of a mobile phase over a stationary phase to effect the separation of analytes of interest. To speed-up and enhance the efficiency of the separation, pressurized mobile phases were introduced. Carbon dioxide-based chromatographic systems use $CO_2$ as a component of the mobile phase, and the $CO_2$ based mobile phase is delivered from pumps and carried through the separation column as a pressurized fluid. In systems using $CO_2$ as a mobile phase component, one challenge is transferring the analyte and ensuring $CO_2$ and co-solvent miscibility downstream of the column. The changes in co-solvent and analyte solubility in the $CO_2$-based mobile phase become especially problematic do to the extreme changes in density experienced when interfacing the $CO_2$-based mobile phase to low pressure detection such as flame ionization detection or mass spectrometry. Therefore, a need exists for chromatography systems that provide increased stability and control of the mobile phase temperature and pressure levels.

BRIEF SUMMARY OF THE TECHNOLOGY

Exemplary embodiments of the present technology are directed to systems for controlling pressure of a mobile phase. Further, the embodiments are related to methodologies, systems and apparatus for that employ multiple pressure control elements to control pressure of a mobile phase. In particular, some embodiments are related to methodologies, systems and apparatus that are used in $CO_2$-based chromatography systems, i.e., a chromatography system in which the mobile phase includes $CO_2$.

In one aspect, the present technology relates to a system of controlling pressure of a mobile phase. The system includes a pumping system disposed to pump a mobile phase including $CO_2$, the pumping system located upstream of a chromatography column. The system also includes a primary pressure control element located downstream of the column and disposed to control pressure within the column. The system also includes a split restrictor located downstream of the primary pressure control element and disposed to divert a portion of a mobile phase flow to a detector. The system also includes a secondary pressure control element located downstream of the split restrictor and disposed to control pressure at the restrictor.

Embodiments of this aspect of the technology can include one or more of the following features. In some embodiments, the primary pressure control element and secondary pressure control element are back pressure regulators. In some embodiments, the split restrictor is a fixed restrictor. In some embodiments, the pressure control devices can be fixed, variable, or thermally-modulated variable restrictors. In some embodiments, the secondary pressure control element controls pressure at the split restrictor such that a constant fraction of the mobile phase is directed to detection. In some embodiments, the detector is a flame ionization detector or a mass spectrometer. In some embodiments, the primary pressure control element is disposed to execute a pressure-controlled gradient separation and the secondary pressure control element is disposed to maintain a constant pressure at the restrictor throughout the gradient. In some embodiments, the primary pressure control element is disposed to maintain constant average density across the column during a composition-programmed gradient separation, and the secondary pressure control element is disposed to maintain a constant pressure at the split restrictor throughout the average density compensation.

In another aspect, the present technology relates to a method of controlling pressure within a $CO_2$-based chromatography system. The method includes pumping a mobile phase including $CO_2$ to a chromatography column. The method also includes controlling pressure within the column using a primary pressure control element located downstream of the column. The method also includes diverting a portion of a mobile phase flow to a detector using a split restrictor located downstream of the primary pressure control element. The method also includes controlling pressure at the split restrictor using a secondary pressure control element located downstream of the split restrictor.

Embodiments of this aspect of the technology can include one or more of the following features. In some embodiments, the primary pressure control element is a back pressure regulator. In some embodiments, the secondary pressure control element is a back pressure regulator. In some embodiments, the split restrictor is a fixed restrictor. In some embodiments, controlling pressure at the restrictor includes controlling pressure such that a constant fraction of the mobile phase is directed to detection. In some embodiments, the detector is a flame ionization detector or a mass spectrometer. In some embodiments, controlling pressure within the column using a primary pressure control element includes executing a pressure-controlled gradient separation, and wherein controlling pressure at the restrictor using a secondary pressure control element includes maintaining a constant pressure at the restrictor throughout the gradient. In some embodiments, controlling pressure within the column using the primary pressure control element includes maintaining a constant average density across the column during a composition-programmed gradient separation, and wherein controlling pressure at the split restrictor using the secondary pressure control element includes maintaining a constant pressure at the split restrictor throughout the average density compensation. In some embodiments, controlling pressure within the column using the primary pressure control element includes maintaining a constant average pressure across the column during a composition-programmed gradient separation. In some embodiments, controlling pressure at the split restrictor using the secondary pressure control element includes maintaining a constant portion of the mobile phase flow directed to the detector in response to a change in viscosity of the mobile phase.

In another aspect, the present technology relates to a method of controlling pressure within a $CO_2$-based chromatography system. The method includes directing a gradient of $CO_2$ and liquid modifier to a $CO_2$-based chromatography column. The method also includes controlling pressure within the column using a primary back pressure regulator located downstream of the column. The method also includes diverting a portion of a mobile phase flow to a detector using a fixed restrictor located downstream of the primary back pressure regulator. The method also includes maintaining constant pressure at the restrictor using a secondary back pressure regulator located downstream of the fixed restrictor in response to an increased percentage of liquid modifier in the gradient.

Embodiments of this aspect of the technology can include one or more of the following features. In some embodiments, the method also includes maintaining the portion of the mobile phase flow diverted to the detector below 1% of the mobile phase flow. In some embodiments, the detector is a flame ionization detector. In some embodiments, the method also includes maintaining the portion of the mobile phase diverted to the detector below about 50% of the mobile phase flow. In some embodiments, the detector is a mass spectrometer. In some embodiments, the method also includes maintaining a constant portion of the mobile phase directed to the detector below about 0.5% of the mobile phase flow. In some embodiments, the detector is a mass spectrometer, and the chromatography system is a preparative-scale chromatographic system.

The above aspects of the technology provide one or more of the following advantages. Some embodiments of the technology allow for increased control of pressure in the chromatography column, and increased control of pressure at a restrictor downstream of the column. Some embodiments of the technology help maintain constant the fraction of the mobile phase that is directed to the detector and help normalize response at the detector for all compounds.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION OF THE TECHNOLOGY

Provided herein are methodologies, systems, and apparatus for controlling pressure of a mobile phase in a $CO_2$-based chromatography system utilizing multiple pressure control elements. Interfacing $CO_2$-based chromatography systems to low pressure detection (e.g., flame ionization detection or mass spectrometry) poses a unique challenge due to the intricacies of managing analyte and co-solvent solubility in carbon dioxide as the mobile phase transitions from a pressurized state to a gas or ambient pressure state. In $CO_2$-based chromatography systems, a fixed restrictor can be used to divert a portion of the mobile phase flow to detection. However, such a restrictor may be unable to adapt to changes in system pressure or fluid composition. As a result of this inability to adapt, any change in system pressure or fluid composition will affect the portion of the mobile phase directed to detection. Any changes in the portion of the mobile phase directed to detection can result in undesirable changes in analyte response.

In one embodiment of the present disclosure, the use of two pressure-controlling elements can allow for a constant fraction of the mobile phase to be directed to detection and ensure a stable and consistent detector signal. In exemplary $CO_2$-based chromatography systems, a fixed restrictor diverts a portion of the total mobile phase flow to a detector. The fixed restrictor also dictates flow based on the dimensions of the restrictor, the pressure drop across the restrictor, and the viscosity of fluid traversing the restrictor. Therefore, any increase in upstream pressure can cause an increase in flow through the restrictor. Viscosity of the fluid also effects the flow rate of fluid traveling through the restrictor. In exemplary embodiments, a first pressure control element is disposed to control the pressure within the $CO_2$-based chromatography column, while a second pressure control element is disposed to control the pressure at a restrictor. The present disclosure addresses the problems associated with a variable split ratio while operating with a pressure-programmed gradient separation, a composition-programmed gradient separation, or while operating in constant-density/pressure mode in $CO_2$-based chromatography systems with a split-flow interface to detection.

Figure 1:
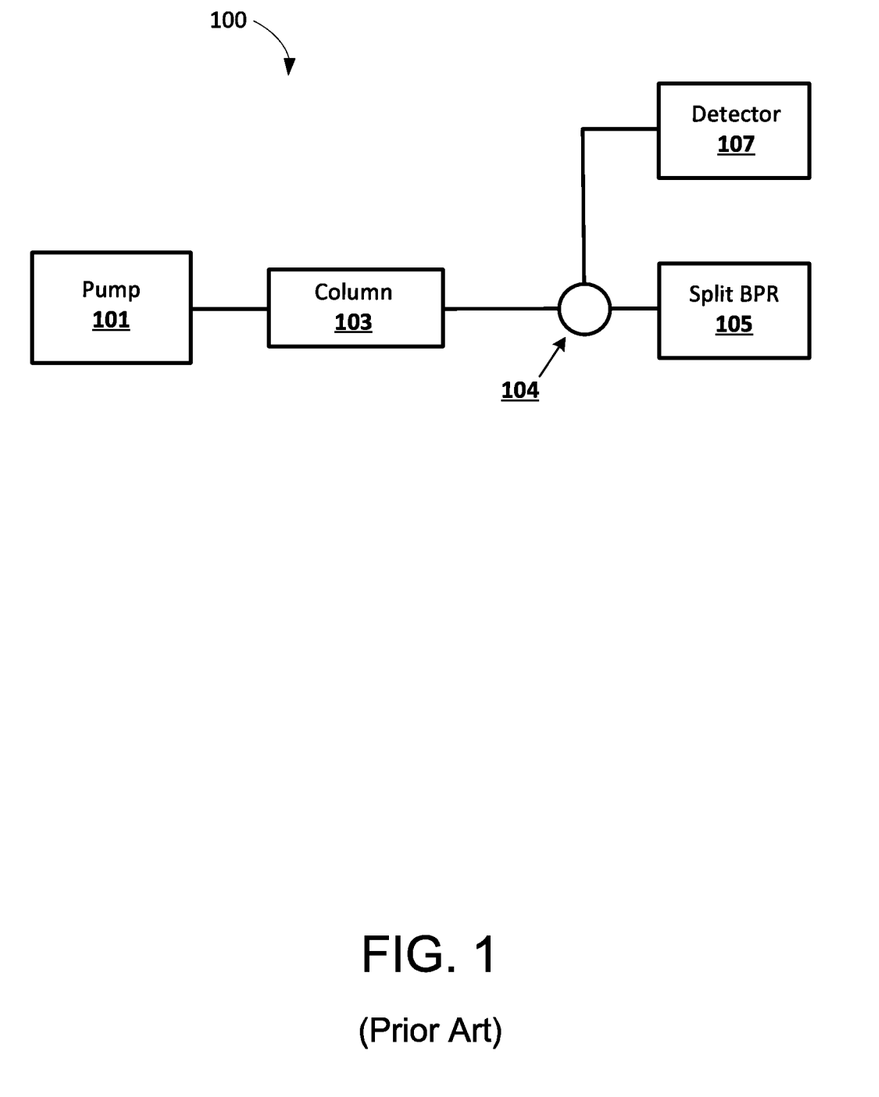
FIG. 1 is a block diagram illustrating an exemplary prior art chromatography system with a single pressure control element.

In prior art systems, in which pressure control had been implemented, undesirable effects have previously been experienced due to the increase in pressure experienced while operating a pressure-programmed gradient separation. For example, any increase in system pressure can increase the mobile phase flow rate directed to detection, which, in turn, can upset the optimized response of the detector to the analyte. FIG. 1 is a block diagram illustrating an exemplary prior art chromatography system 100 with a single pressure control element. In this example, a pump 101 is used to pump a mobile phase to a chromatography column 103. Downstream of the column 103, a restrictor 104 diverts a portion of the total mobile phase exiting the column 103 to a detector 107. A back pressure regulator 105 is used to control both the post-column pressure and the pressure at the head of the restrictor 104. In some examples, the detector 107 is a flame ionization detector, and a fixed restrictor 104 is used as an interface to a flame ionization detector to direct a small portion of the total mobile phase flow to the detector 107. Since flame ionization detection often does not tolerate any amount of organic modifier in the system, a pressure-programmed gradient can be employed to increase the peak capacity of such separations. When employing a single pressure control element in a $CO_2$-based chromatography system, the increase in pressure experienced while operating the pressure-programmed gradient separation causes an increase in the flow through the restrictor 104. Since the chromatographic pump 101 is operating in constant-pressure mode, the increased split flow causes a change in the fraction of total mobile phase directed to the detector 107.

Figure 2:
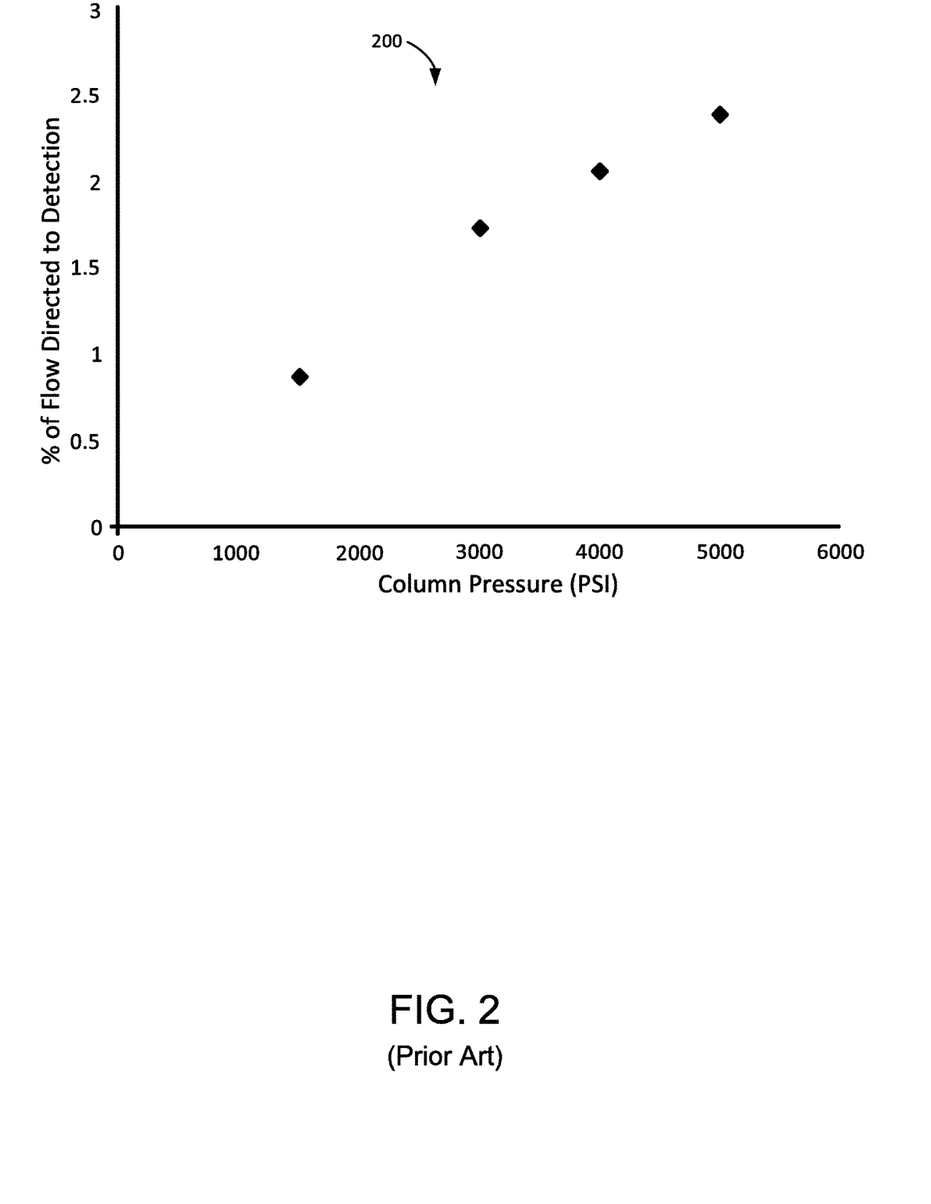
FIG. 2 is a graph of the portion of mobile phase flow directed to detection using the exemplary prior art chromatography system of FIG. 1.

FIG. 2 is a graph 200 of the percentage of mobile phase flow directed to detection using a single pressure control element (i.e., the system 100 shown in FIG. 1). As seen in this figure, increased system pressure causes an increase in the percentage of mobile phase flow directed to the detector. In this particular example, the percent of mobile phase flow directed to detection increases from below 1% to above 2.5% as the pressure increases to 5,000 PSI. In the case of flame ionization detection, which is a mass-sensitive detector, any increase in the portion of the mobile phase (i.e. increase in the portion of the analyte) directed to the detector can cause an increase in signal generated. Therefore, flame ionization detection will experience greater response for late eluting compounds. This effect is undesirable since one of the most advantageous features of flame ionization detection is its universal response to carbon. Further, a change in the portion of the mobile phase directed to the detector will warrant changes in the optimal detector settings. Such changes in the portion of the mobile phase directed to detection without changing the detector settings may result in less than optimal response of the analyte. In extreme cases, the detector may not be able to adapt to very large changes in the portion of the mobile phase directed to detection, which may result in no generated signal at all.

Systems and methods of the present technology are advantageous because they allow for increased control of both the pressure in the chromatography column as well as the pressure at the restrictor. In general, the systems and methods feature two pressure control elements positioned to overcome the varying response of flame ionization detection over a pressure-programmed gradient separation. In exemplary embodiments, a first pressure control element is positioned downstream of the $CO_2$-based chromatography column to maintain pressure within the column at a desired level, while the second pressure control element is located downstream of a split restrictor in order to maintain pressure at the split restrictor at a desired level. Such techniques help maintain the fraction of the mobile phase directed to the detector at a constant level and prevent an increased response at the detector for late eluting compounds.

Figure 3:
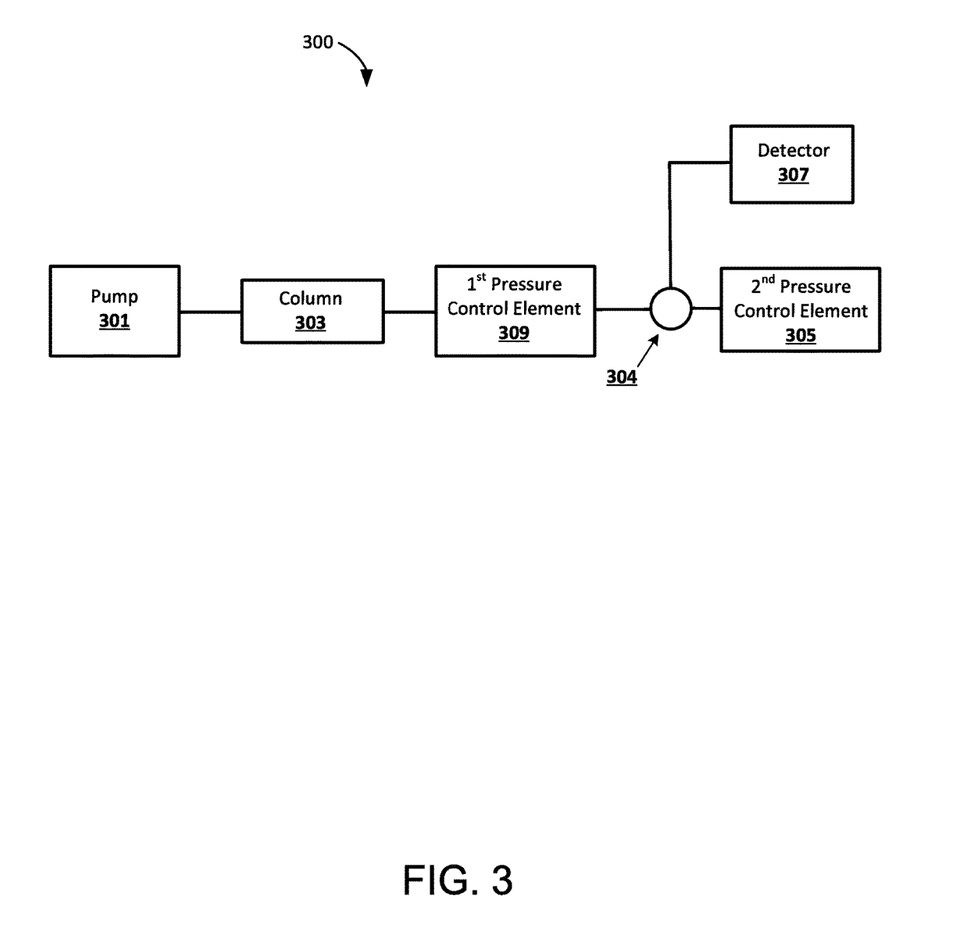
FIG. 3 is a block diagram illustrating an exemplary $CO_2$-based chromatography system including two pressure control elements, according to an embodiment of the present disclosure.

FIG. 3 is a block diagram 300 illustrating an exemplary $CO_2$-based chromatography system including two pressure control elements, according to an embodiment of the present disclosure. In this example, a pump 301 is used to pump a mobile phase containing $CO_2$ to a chromatography column 303. A first pressure control element 309 is located downstream of the column 303 and is responsible for maintaining pressure within the column 303. The first pressure control element 309 can also be responsible for executing the pressure-programmed gradient. Downstream of the first pressure control element 309, a split restrictor 304 diverts a portion of the total mobile phase exiting the column 303 to a detector 307. In some examples, the detector 307 is a flame ionization detector or a mass spectrometer. A second pressure control element 305 is used to maintain a constant pressure at the head of the split restrictor 304 over the course of the separation. In exemplary embodiments, the first pressure control element 309 and the second pressure control element 305 are back pressure regulators. As a result of employing two pressure control elements 309 and 305, the portion of the mobile phase directed to the detector 307 by the split restrictor 304 is normalized over the course of a pressure-programmed gradient separation. In some embodiments, the split restrictor 304 is a fixed restrictor. As will be appreciated, any number of pressure control elements or flow-varying devices can be used instead of a back pressure regulator. For example, a fixed, variable, or thermally-modulated variable restrictor could also be used as the pressure control elements 309 and 305.

Figure 4:
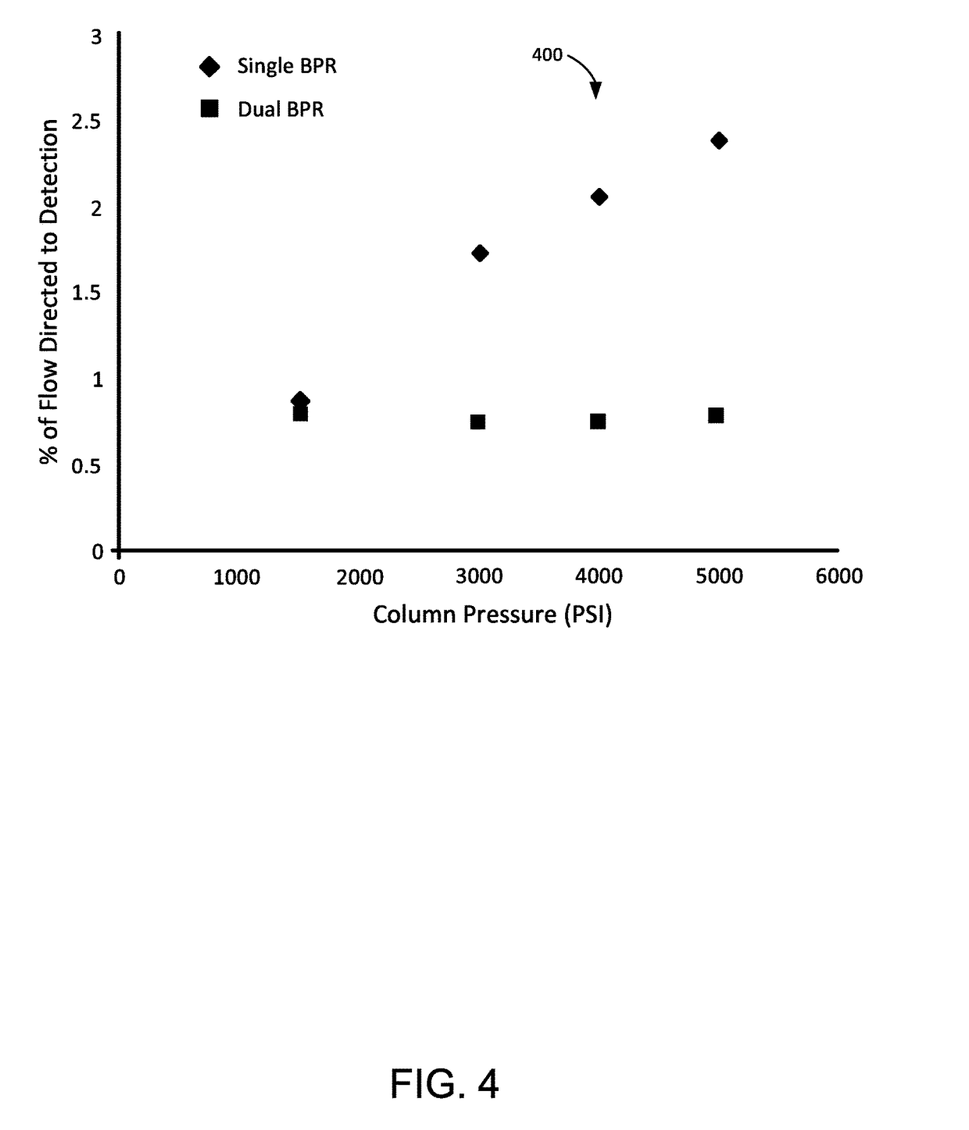
FIG. 4 is a graph of the portion of mobile phase flow directed to detection using a single pressure control element and using two pressure control elements.

FIG. 4 is a graph 400 showing the relationship between column pressure and percentage of mobile phase flow directed to a detector for a $CO_2$-based chromatography system using a single pressure control element and a $CO_2$-based chromatography system using two pressure control elements. As seen in this figure, the diamond shapes represent a system containing a single pressure control element and show the portion of mobile phase flow directed to detection increasing with the column pressure. This is similar to the example described above in reference to FIG. 2. Alternatively, the square shapes represent the relationship between column pressure and percentage of mobile phase flow directed to a detector for a $CO_2$-based chromatography system using two pressure control elements. This example embodiment shows a steady portion of the mobile phase flow directed to detection over a range of column pressures. In addition to operating with neat $CO_2$, such as is the case with flame ionization detection, two pressure control elements can also maintain a constant split ratio while operating with a variable column pressure and a modifier. Such a system may be designed to maintain constant average density along the column or to compensate for changes in column density when operating a temperature-programmed gradient separation. Furthermore, a system containing multiple pressure control elements can normalize variable split ratios when operating a composition-programmed gradient separation. With a single pressure control element, the portion of the mobile phase directed to detection will change as the viscosity of the mobile phase is altered over the course of a composition-programmed gradient separation.

Figure 5:
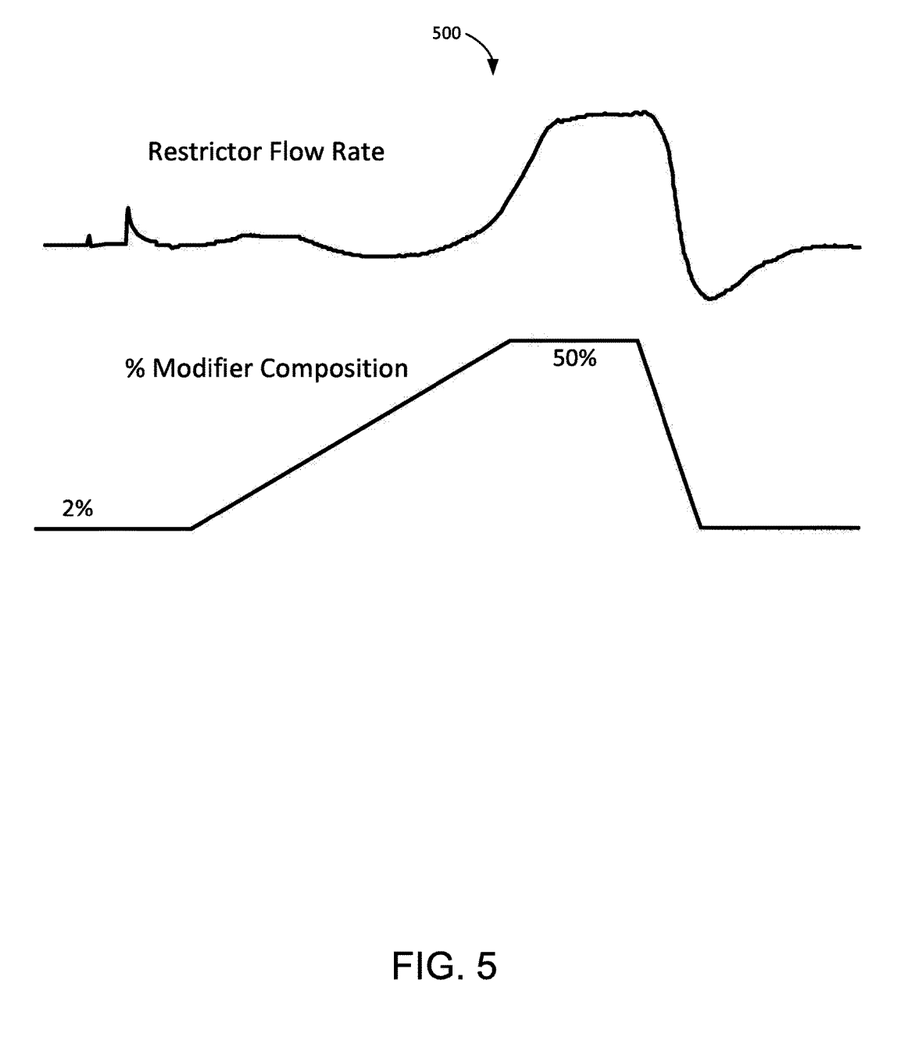
FIG. 5 is a graph of the restrictor flow rate over a composition-programmed gradient separation.

FIG. 5 is a graph 500 of the restrictor flow rate over a composition-programmed gradient separation employing a $CO_2$ and methanol mobile phase. As seen in this figure, the smallest portion of the mobile phase is directed to detection when the restrictor flow rate is lowest at approximately 30% modifier composition, when the composition promotes turbulent flow through the restrictor. The largest portion of the mobile phase is directed to detection at 50% modifier composition, when the fluid properties promote laminar flow through the restrictor. Alternatively, a system containing two pressure control elements can normalize this variable split ratio. The first pressure control device can be responsible for maintaining the desired pressure at the outlet of the column, while the second can be programmed to normalize the split ratio. For example, the second pressure control element can increase the pressure at the head of the restrictor at 30% modifier and proportionally decrease the pressure at the head of the restrictor as the composition of the mobile phase approaches 50% modifier. In this fashion, the split ratio can be maintained constant over a broad composition-programmed gradient separation.

Figure 6:
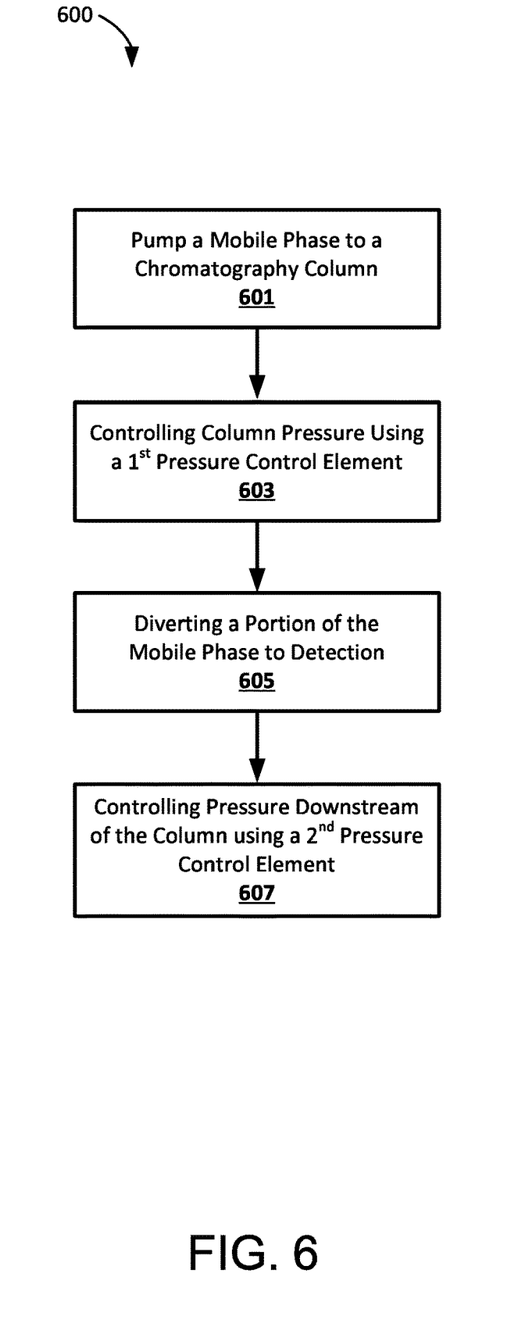
FIG. 6 is a flow chart of an exemplary method for controlling pressure in a $CO_2$-based chromatography system, according to an embodiment of the present disclosure.

FIG. 6 is a flow chart 600 of an exemplary method for controlling pressure in a $CO_2$-based chromatography system, according to an embodiment of the present disclosure. In step 601, a pump is used to pump a mobile phase containing $CO_2$ to a chromatography column.

In step 603, a first pressure control element is used to control pressure within the $CO_2$-based chromatography column. The first pressure control element is located downstream of the chromatography column and can also be responsible for executing a pressure-programmed gradient.

The first pressure control element can be, for example, a back pressure regulator, a variable restrictor, or a thermally modulated variable restrictor.

In step 605, a portion of the mobile phase flow is directed to detection. In some embodiments, a split restrictor can be located downstream of the first pressure control element and disposed to divert a portion of the mobile phase flow to a detector. As discussed above, the detector can be a flame ionization detector or a mass spectrometer, in various embodiments.

In step 607, a second pressure control element is used to control the pressure downstream of the column at the restrictor. As discussed above, interfacing $CO_2$-based chromatography systems to low pressure detection (e.g., flame ionization detection or mass spectrometry) poses a unique challenge due to the intricacies of managing analyte and co-solvent solubility in carbon dioxide as the mobile phase transitions from a pressurized state to a gas or ambient pressure state. In exemplary embodiments, the use of two pressure control elements allows for the portion of the mobile phase directed to the detector to be normalized over the course of a pressure-programmed gradient separation or a composition-programmed gradient separation.

The second pressure control element can control pressure at the split restrictor such that a constant fraction of the mobile phase flow is directed to detection. In exemplary embodiments, the second pressure control element is disposed to maintain a constant pressure at the restrictor while the first pressure control element executes a pressure-controlled gradient separation. In alternative embodiments, the second pressure control element is disposed to maintain a constant pressure at the split restrictor while the first pressure control element maintains a constant average density across the column during a composition-programmed gradient separation. In exemplary embodiments, the combination of a first pressure control element and a second pressure control element can maintain the portion of the mobile phase flow diverted to the detector below about 1% of the total mobile phase flow. In alternative embodiments, the combination of a first pressure control element and a second pressure control element can maintain the portion of the mobile phase flow diverted to the detector below about 50% of the total mobile phase flow. In another embodiment, the combination of a first pressure control element and a second pressure control element can maintain the portion of the mobile phase flow diverted to the detector below about 0.5% of the total mobile phase flow. In various embodiments, the second pressure control element can be, for example, a back pressure regulator, a fixed restrictor, a variable restrictor, or a thermally modulated variable restrictor.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

In alternative embodiments, the techniques described above with respect to pumps used in $CO_2$-based chromatography systems may be applicable to pumps used in other types of chromatography systems that include mobile phases that vary greatly in density with minor changes in temperature. For example, a mobile phase including methanol at extremely high pressures may in some instances benefit from added temperature control. In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

What is claimed is:

1. A system of controlling pressure downstream of a $CO_2$-based chromatography column, the system comprising:
   a pumping system disposed to pump a mobile phase including $CO_2$, the pumping system located upstream of a chromatography column;
   a primary pressure control element located downstream of the column and disposed to control pressure within the column;
   a split restrictor located downstream of the primary pressure control element and disposed to divert a portion of a mobile phase flow to a detector; and
   a secondary pressure control element located downstream of the split restrictor and disposed to control pressure at the restrictor.

2. The system of claim 1, wherein the primary pressure control element and secondary pressure control element are back pressure regulators.

3. The system of claim 1, wherein the split restrictor is a fixed restrictor.

4. The system of claim 1, wherein the secondary pressure control element controls pressure at the split restrictor such that a constant fraction of the mobile phase flow is directed to detection.

5. The system of claim 1, wherein the detector is a flame ionization detector or a mass spectrometer.

6. The system of claim 1, wherein the primary pressure control element is disposed to execute a pressure-controlled gradient separation and the secondary pressure control element is disposed to maintain a constant pressure at the restrictor throughout the pressure-controlled gradient separation.

7. The system of claim 1, wherein the primary pressure control element is disposed to maintain constant average density across the column during a composition-programmed gradient separation, and the secondary pressure control element is disposed to maintain a constant pressure at the split restrictor throughout an average density compensation.

8. The system of claim 1, wherein the primary pressure control element is disposed to maintain constant average pressure across the column during a compensation-programmed gradient separation, and the secondary pressure control element is disposed to maintain a constant pressure at the split restrictor throughout an average density compensation.

9. The system of claim 1, wherein the primary pressure control element is disposed to maintain pressure across the column during a composition-programmed gradient separation, and the secondary pressure control element is disposed to maintain a constant portion of the mobile phase flow directed to detection throughout an average changing mobile phase composition.

10. A method of controlling pressure within a $CO_2$-based chromatography system, the method comprising:
   pumping a mobile phase including $CO_2$ to a chromatography column;
   controlling pressure within the column using a primary pressure control element located downstream of the column;
   diverting a portion of a mobile phase flow to a detector using a split restrictor located downstream of the primary pressure control element; and
   controlling pressure at the split restrictor using a secondary pressure control element located downstream of the split restrictor.

11. The method of claim 10, wherein the primary pressure control element is a back pressure regulator.

12. The method of claim 11, wherein the secondary pressure control element is a back pressure regulator.

13. The method of claim 10, wherein the split restrictor is a fixed restrictor.

14. The method of claim 10, wherein controlling pressure at the restrictor includes controlling pressure such that a constant fraction of the mobile phase flow is directed to detection.

15. The method of claim 10, wherein the detector is a flame ionization detector or a mass spectrometer.

16. The method of claim 10, wherein controlling pressure within the column using a primary pressure control element includes executing a pressure-controlled gradient separation, and wherein controlling pressure at the restrictor using a secondary pressure control element includes maintaining a constant pressure at the restrictor throughout the pressure-controlled gradient separation.

17. The method of claim 10, wherein controlling pressure within the column using the primary pressure control element includes maintaining a constant average density across the column during a composition-programmed gradient separation, and wherein controlling pressure at the split restrictor using the secondary pressure control element includes maintaining a constant pressure at the split restrictor throughout an average density compensation.

18. The method of claim 10, wherein controlling pressure within the column using the primary pressure control element includes maintaining a constant average pressure across the column during a composition-programmed gradient separation, and wherein controlling pressure at the split restrictor using the secondary pressure control element includes maintaining a constant pressure at the split restrictor throughout an average pressure compensation.

19. The method of claim 10, wherein controlling pressure at the split restrictor using the secondary pressure control element includes maintaining a constant portion of the mobile phase flow directed to the detector in response to a change in viscosity of the mobile phase flow.

20. A method of controlling pressure within a $CO_2$-based chromatography system, the method comprising:
   directing a gradient of $CO_2$ and liquid modifier to a $CO_2$-based chromatography column;
   controlling pressure within the column using a primary back pressure regulator located downstream of the column;
   diverting a portion of a mobile phase flow to a detector using a fixed restrictor located downstream of the primary back pressure regulator; and
   maintaining pressure at the restrictor using a secondary back pressure regulator located downstream of the fixed restrictor in response to an increased percentage of liquid modifier in the gradient.

21. The method of claim 20, further comprising maintaining the portion of the mobile phase diverted to the detector below about 50% of the mobile phase flow.

22. The method of claim 21, wherein the detector is a mass spectrometer.

* * * * *